United States Patent [19]

Krsek

[11] Patent Number: 5,049,683
[45] Date of Patent: Sep. 17, 1991

[54] PROCESS FOR THE PRODUCTION OF ALPHA-6-DEOXYTETRACYCLINES

[75] Inventor: George Krsek, Culver, Ind.
[73] Assignee: Houba, Inc., Culver, Ind.
[21] Appl. No.: 552,839
[22] Filed: Jul. 12, 1990

Related U.S. Application Data

[63] Continuation of Ser. No. 293,224, Jan. 4, 1989, abandoned.

[51] Int. Cl.$^5$ ............................................. C07C 103/75
[52] U.S. Cl. .................... 550/206; 552/207
[58] Field of Search ............... 260/351.5; 552/206, 552/207

[56] References Cited

U.S. PATENT DOCUMENTS

| | | | |
|---|---|---|---|
| 2,984,686 | 5/1961 | Blackwood et al. | 260/351.5 |
| 3,200,149 | 8/1965 | Blackwood et al. | 260/351.5 |
| 3,444,198 | 5/1969 | Korst | 260/351.5 |
| 3,550,096 | 10/1985 | Page et al. | 502/166 |
| 3,907,890 | 9/1975 | Scenio | 260/351.5 |
| 3,954,862 | 5/1976 | Morris, Jr. | 260/351.5 |
| 3,962,131 | 6/1976 | Faubl et al. | 252/429 R |
| 3,962,331 | 6/1976 | Cotti | 260/351.5 |
| 4,001,321 | 1/1977 | Faubl | 260/351.5 |
| 4,207,258 | 1/1980 | Broggi et al. | 260/351.5 |
| 4,597,904 | 7/1986 | Page | 260/351.5 |
| 4,743,699 | 5/1986 | Page et al. | 556/23 |

FOREIGN PATENT DOCUMENTS

2216268  8/1974  France ............... 260/351.5

OTHER PUBLICATIONS

Czakova, J., Mol. Catl., II (1981), pp. 313-322.
Hartley, Supported Metal Complexes, D. Reidel Publishing Co., 1985, pp. 148-171.
Kochloefl et al., JCS S. Chem. Comm., 1977, pp. 510-511.
Barthalin et al, Mol. Catalysis (I), 1976, pp. 375-382.
Yuffa et al., Russian Chemical Reviews, 55 (9), 1986, pp. 825-841.

Primary Examiner—C. Warren Ivy
Assistant Examiner—Raymond Covington
Attorney, Agent, or Firm—Bryan, Cave, McPheeters & McRoberts

[57] ABSTRACT

A process for the preparation of alpha-6-deoxytetracyclines from the corresponding 6-methylenetetracyclines is described using a silica-supported heterogeneous rhodium catalyst:

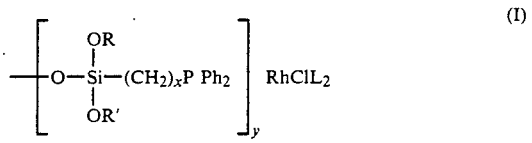

(I)

The process stereospecifically produces the alpha epimers at higher yields while using lower rhodium metal levels than prior methods.

4 Claims, No Drawings

PROCESS FOR THE PRODUCTION OF ALPHA-6-DEOXYTETRACYCLINES

This is a continuation of U.S. application Ser. No. 07/293,224, filed Jan. 4, 1989, now abandoned.

This invention relates to a process for the preparation of alpha-6-deoxytetracyclines and to the use of a heterogeneous rhodium catalyst therein, and more particularly to such a process useful in the production of the antibiotic doxycycline, viz., alpha-6-deoxy-5-oxytetracycline.

BACKGROUND OF THE INVENTION

The preparation of doxycycline and other alpha-6-deoxytetracyclines was first described in Blackwood et al. U.S. Pat. No. 3,200,149 granted Aug. 10, 1965. That patent described their preparation by the catalytic hydrogenation of a corresponding 6-methylene intermediate, e.g., in the case of doxycycline, 11a-chloro-6-deoxy-6-demethyl-6-methylene-5-oxytetracycline (11a-chloro methacycline) or 6-deoxy-6-demethyl-6-methylene-5-oxytetracycline (methacycline), in the presence of a heterogeneous noble metal catalyst, e.g. palladium on carbon. The Blackwood patent disclosed the production, in yields of up to about 50%, of equimolar proportions of the diastereoisomers (epimers) of the 6-deoxytetracyclines. In the case of doxycycline, the patent disclosed the co-production of the corresponding beta epimer, beta-6-deoxy-5-oxytetracycline.

Subsequent efforts have been directed to the development of syntheses for producing the 6-deoxytetracyclines in greater yields and with greater stereoselectivity of formation of the desired alpha epimers, e.g., doxycycline. Thus, Korst U.S. Pat. No. 3,444,198 granted May 13, 1969, disclosed that the stereoselectivity of formation of the alpha epimers may be increased when the noble metal hydrogenation catalyst is poisoned. The Korst patent described the formation of epimeric mixtures of the 6-deoxytetracyclines in total yields of up to about 60%, with the stereoselective production of the alpha epimers in amounts of up to about 90% of the epimeric product mixtures.

The use of rhodium chloride/triphenylphosphine and similar complexes as homogeneous, stereospecific hydrogenation catalysts in the production of doxycycline and other alpha-6-deoxy-5-oxytetracyclines has also been extensively discussed in the patent literature. See, for example, U.S. Pat. Nos. 3,907,890; 3,962,331; 4,001,321; 4,207,258; 4,550,096; 4,743,699; and French Patent No. 2,216,268.

Other noble metal or noble metal salt heterogeneous hydrogenation catalysts for 6-methylenetetracyclines have also been disclosed in the literature. For example, Faubl et al. in U.S. Pat. No. 3,962,131 describes a heterogeneous catalyst for use in hydrogenating methacycline. The Faubl catalyst is produced by reacting rhodium trichloride and sodium acetate in methanol at temperatures in excess of 50° C., and reacting this system with triphenylphosphine. The Faubl catalyst is reported to exhibit stereoselectivity for the alpha epimers by a factor of at least 9:1 versus the beta epimer with a yield of 98.8% reported in the sole Faubl example.

Catalytic hydrogenation of methacycline using a catalytic amount of rhodium metal together with a phosphine, preferably triphenylphosphine, and a promoter, e.g., excess acid (over that required to form an acid addition salt with methacycline), is disclosed by Morris, Jr. in U.S. Pat. No. 3,954,862. The heterogeneous rhodium metal catalyst may be of the non-supported or supported type, e.g., supported by carbon, silica, alumina or barium sulfate.

Another process for the heterogeneous hydrogenation of methacycline is disclosed by Page in U.S. Pat. No. 4,597,904. Page employs a rhodium salt catalyst wherein the rhodium is bonded to a polysiloxane carrier, generally an aminopolysiloxane. The methacycline hydrogenation is accomplished in the presence of a tertiary phosphine, e.g., triphenylphosphine. The Page hydrogenation process is reported to be sterospecific, typically yielding less than 0.2% beta epimer. However, polysiloxane materials are known to be sensitive to elevated temperatures, e.g., greater than 90° C., and any breakdown of the polysiloxane carrier would adversely impact the functionality and the recylability of the Page rhodium salt catalyst.

The present invention is directed to an improved process for the production of doxycycline and other alpha-6-deoxytetracyclines, wherein the desired alpha epimer is produced in both high yield and stereospecificity, and the noble metal constituent of the hydrogenation catalyst may be utilized in smaller proportions than heretofore required and is readily recoverable from the reaction mixture for reuse. Other objects and advantages of this invention will be apparent from the following description of preferred embodiments thereof.

SUMMARY OF THE INVENTION

This invention comprises an improved process for the preparation of alpha-6-deoxy-tetracyclines by the hydrogenation of the corresponding 6-methylenetetracyclines in the presence of a heterogeneous rhodium catalyst wherein the rhodium is complexed and bound to a silica gel support.

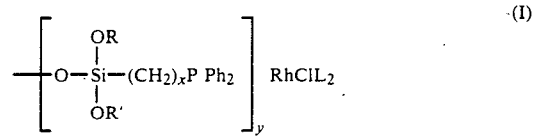

Silica-supported rhodium complex catalysts of this type have been disclosed for the halogenation of alkenes. Czakova et al., *J. Mol. Catal. II*, 313–322 (1981). See also Hartley, *Supported Metal Complexes*, D. Reidel Publishing Co., pages 150 et seq. (1985); Kochloefl et al., *J.C.S. Chem. Comm.*, 1977, 510–11; Conan et al., *J. Mol. Catal. I*. 375–382 (1976).

It has been found that when an appropriate 6-methylenetetracycline substrate is hydrogenated in the presence of a heterogeneous rhodium catalyst of the preceding type, the corresponding alpha-6-deoxytetracycline is produced in greater than about 95% yield and with the co-production of negligible amounts of the corresponding beta-6-deoxytetracycline epimer. The heterogeneous rhodium catalyst is also easily recovered from the reaction system, e.g., by filtration, thereby allowing for the efficient reuse of catalyst in subsequent hydrogenation reactions, and for the elimination of expensive purification operations generally required for separation of the undesired beta epimers.

Moreover, it has been found that the above heterogeneous rhodium catalyst may be used to stereospecifically hydrogenate methacycline to form the alpha epimer doxycycline at significantly lower rhodium metal levels as compared to prior art heterogeneous catalyst systems. According to the present invention, stereospecific formation of doxycycline is achieved at rhodium metal levels of as low as 0.15 mg per gram 11-a chloro methacycline, without sacrificing product yield. Indeed, yields well above 90% and as high as 99.3% are achieved at rhodium metal levels no higher than 0.2 mg/g methacycline. By way of comparison, the lowest reported rhodium metal methacycline ratio for the Page heterogeneous catalyst was 0.25 mg/gram (Example 1) with a yield of only 87.4%. Similarly, at a rhodium metal 11-a chloro methacycline ratio of 0.19 mg/gram (Example 6) a yield of only 89.9% was achieved using a Page heterogeneous catalyst. Still higher rhodium metal levels are reported for the Morris, Jr. heterogeneous catalyst system (2.3 and 23 mg/gram). Thus, dramatic reductions in the amount of rhodium metal required to selectively form alpha-6-deoxytetracyclines may be achieved at high yields with the attendant cost advantages. Comparisons of the noble metal levels in prior art hydrogenation catalysts and their respective yields and stereospecificities as compared to the process of the present invention are presented in the following Table (prior art data taken from U.S. Pat. No. 4,597,904 to Page; Table I).

alkoxysilyl-substituted alkyldiphenyl phosphines such as the following:
$(EtO)_3SiCH_2PPh_2$
$(EtO)_3Si(CH_2)_2PPh_2$
$(EtO)_3Si(CH_2)_2PPh_2$
$(EtO)_3Si(CH_2)_4PPh_2$
$(EtO)_3Si(CH_2)_5PPh_2$
$(EtO)_3Si(CH_2)_6PPh_2$
$(EtO)_2MeSiCH_2PPh_2$
$(EtO)_2MeSi(CH_2)_2PPh_2$
$(EtO)_2MeSi(CH_2)_3PPh_2$
$(EtO)Me_2SiCH_2PPh_2$
wherein Et is ethyl and Ph is phenyl. Alternatively, ligands may be formed in situ with the silica gel, e.g., by reacting chloromethyl ether and diphenylphosphine lithium.

The silica gel used in preparing the catalyst generally has a particle size of 0.063 to 0.2 mm and a pore diameter of 20 to 100 Angstroms, e.g., Kieselgel 100 (Merck). Preferably, the silica gel has a particle size of 0.063 to 0.090 mm and a pore size of 40 to 60 Angstroms.

The silica gel is generally dried, e.g., in a vacuum oven at 180° C., before being reacted with an alkoxysilyl-substituted alkyldiphenyl phosphine. The reaction of the silica gel with the alkyldiphenyl phosphines is generally accomplished in an aromatic solvent, e.g., benzene, xylene or toluene, at a temperature of from 60 to 115° C. For example, the dried silica gel may be added to the aromatic solvent under an inert gas blanket, e.g., nitrogen, together with 2-diphenyl phosphine-ethyltriethoxysilane to attach suitable ligands to the silica gel. The reaction mixture is generally refluxed for about one to six hours to allow the ligands to attach to the silica gel.

The reaction mixture is then azeotropically distilled to remove ethanol formed by interaction between the alkoxysilane group of the ligand compound and the surface hydroxyl groups of the gel support. Distillation conditions depend on the solvent employed and whether the reaction is done under ambient pressures or under vacuum, as will be readily apparent to one of ordinary skill in the art.

Typically, after the distillate is removed, fresh make-up solvent is added to the reaction mixture and the system is agitated under an inert atmosphere, e.g., nitrogen, while cooling to 20° to 30° C. The reaction mixture

TABLE

| PATENT | EXAMPLE | STARTING MATERIAL | NOBLE METAL | NOBLE METAL LEVEL (mg/g methacycline or 11a-chloro) | STOICHIOMETRIC YIELD | ANALYSIS OF PRODUCT | | |
|---|---|---|---|---|---|---|---|---|
| | | | | | | $\alpha$-epimer | $\beta$-epimer | Methacycline |
| Blackwood | 32 | methacycline | Rh | 50.0 | 45.8% | 50% | 50% | |
| (U.S. Pat. No. 3,200,149) | 33 | methacycline HCl | Rh | 27.1 | 88.0% | 21.8%% | 9.4% | 23.5% |
| Morris, Jr. | 3 | methacycline HCl | Rh | 2.3 | NI | 81.0%* | 1.6%* | — |
| (U.S. Pat. No. 3,954,862) | 4 | methacycline HCl | Rh | 23.0 | NI | 80.0%* | 1.5%* | — |
| | 6 | 11a-chloro methacycline pts | Ph | 20.3 | 71.5% | 55.5% | 1.8%* | 2.0% |
| | 17 | 11a-chloro methacycline pts | Rh | 2.1 | 86.7% | 59.9% | 1.33% | 0.8% |
| Page | 1 | methacycline HCl | Rh | 0.25 | 87.4% | 99.6% | 0.2% | — |
| (U.S. Pat. No. 4,597,904) | 4 | methacycline HCl | Rh | 0.41 | 99.1% | 99.5% | 0.2% | — |
| | 6 | 11a-chloro methacycline pts | Rh | 0.19 | 89.9% | 99.5% | 0.1% | — |
| | 10 | methacycline HCl | Rh | 0.37 | 91.4% | 99.5% | 0.2% | 0.1% |
| | 13 | 11a-chloro methacycline pts | Rh | 0.38 | 90.1% | 99.7% | 0.2% | — |
| Present Invention | 3 | 11a-chloro methacycline pts | Rh | 0.15 | 94.0% | 99.2% | 0.1% | — |
| | 2 | methacycline HCl | Rh | 0.20 | 99.0% | 99.4% | 0.1% | — |
| | 5 | methacycline HCl | Rh | 0.20 | 99.3% | 99.4% | 0.1% | — |

NI — not indicated
*Content from analysis of the reaction mixture

The method of the present invention thus stereospecifically produces the alpha epimer at significantly higher yields than those reported for prior art processes with the exception of Page example 4. However, in the case of Page example 4, the ratio of rhodium to methacycline HCl was more than twice that employed according to the present invention. Accordingly, the present invention is more efficient than prior art processes for preparing alpha-6-deoxycyclines.

PREFERRED EMBODIMENTS OF THE INVENTION

The catalysts useful in the hydrogenation process of the invention are preferably prepared by reacting silica gel with a compound having one or more groups capable of functioning as ligands which bond rhodium complexes thereto. It is believed that the length and mobility of the ligands influence the degree to which catalytic intermediates interact, thereby reducing hydrogenation activity. Compounds having suitable groups include is then filtered and the recovered cake is washed with solvent. The filter cake comprises silica gel with a plurality of ligands attached thereto, the free ends of the ligands being suitable for attachment to a rhodium complex.

The filter cake is reslurried in an aromatic solvent and a rhodium complex is added thereto. For example suitable rhodium complexes include $Rh_2Cl_2(C_2H_4)_4$, $Rh_2cl_2$ (cyclooctene)$_4$, $RhCl_2(PPh_3)$, Wilkinson's Catalyst $[Rh(PPh_3)_3Cl]$.

The rhodium complex-containing system is lightly refluxed under an inert atmosphere to allow the rhodium complex to react with the free ends of the ligand groups, e.g., for 12 to 16 hours. The reaction mixture is then cooled to 20–40° C. and filtered to recover the heterogeneous rhodium catalyst of the invention. The catalyst generally has from 0.3 to 0.6% rhodium metal per gram of catalyst.

In accordance with the invention, the heterogeneous rhodium catalyst is utilized in the production of any of the known alpha-6-deoxytetracyclines, preferably those having the formula:

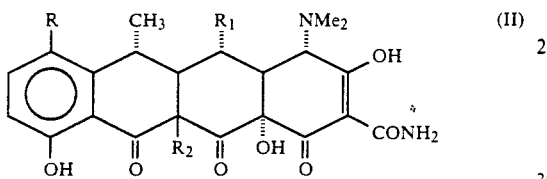

wherein R and $R_2$ are each hydrogen or chloro and $R_1$ is hydrogen or hydroxyl.

The preceding compounds are produced by hydrogenation of the corresponding 6-methylene tetracycline compounds of the formula:

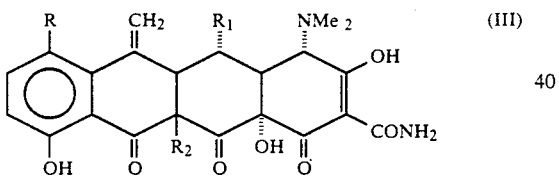

wherein R, $R_1$ and $R_2$ are as defined above.

6-methylenetetracyclines which are thus reacted may be prepared in the manner known in the art, e.g., as described in Blackwood U.S. Pat. No. 2,984,986 granted May 16, 1961 or Villax U.S. Pat. No. 3,848,491 granted Nov. 19, 1974.

Preferably, the catalytic hydrogenation is utilized to prepare doxycycline (wherein R is hydrogen and $R_1$ is hydroxyl) from methacyline (wherein R is hydrogen, $R_1$ is hydroxyl and $R_2$ is hydrogen) or from 11a-chloro methacycline (wherein R is hydrogen, $R_1$ is hydroxyl, and $R_2$ is chloro). When 11a-chloro methacycline is utilized as the starting material, an equimolar quantity of triphenyl phosphine is also typically included in the hydrogenation system.

The hydrogenation reaction is carried out in one of the manners known in the art, with the stereospecific formation of the desired alpha epimer in yields in excess of 94%. HPLC analyses of the hydrogenation products generally indicate negligible beta-epimer contents. The hydrogenation is effected in the presence of from about 0.05 to 0.2 grams of catalyst per gram of 6-methylenetetracycline reacted, which corresponds, for example in the production of doxycycline, to a rhodium metal to methacycline ratio of 0.15 to 1.2 mg per gram. The amount of rhodium required for reduction of methacycline to doxycycline may thus be significantly reduced as compared to prior art hydrogenation processes. The catalytic hydrogenation of the present invention therefore provides superior yields and purities of the desired alpha-6-deoxytetracyclines, with substantially improved efficiencies in the operation.

The reaction is suitably carried out in a lower alkanolic solvent. Preferably methanol or ethanol is employed. The solvents are typically degassed with nitrogen prior to use.

The reaction time depends on the amount of catalyst and the type of autoclave used for hydrogenation. Normally, to obtain high yields and purities, reaction times of from about 6 to 12 hours are utilized. It is preferred, but not critical, to carry out the reaction under pressures ranging from about 60 to 130 psig, and at temperatures of from about 90° to 100° C. At temperatures lower than about 85° C. the reaction may be unacceptably slow, and at higher temperatures decomposition can occur.

Addition of a small amount of triphenylphosphine, e.g., from about 4 to 8 mg per gram of the 6-methylenetetracycline substrate, to the reaction mixture prior to hydrogenation promotes and accelerates the rate of hydrogen absorption, thus facilitating completion of the reaction. The optimum quantity of triphenylphosphine for a given catalyst is determined empirically. A small amount of acid, e.g., hydrochloric acid, may also be added to promote the hydrogenation reaction.

The doxycycline or other alpha-epimer is typically crystallized as an acid addition salt from the reaction mixture, e.g., in the form of the p-toluene sulfonate, sulfosalicylate, or hydrochloride salt. The purity is more than 99.5% by HPLC. The doxycycline acid addition salt is thereafter converted directly to doxycycline hyclate (the hemiethanolate hemihydrate) in stoichiometric yield by procedures known in the art.

The catalytic hydrogenation may be utilized in a single step to effect both the reductive dehalogenation and reduction of the 6-methylene group of an 11a-halo-6-deoxy-6-demethyl-6-methylenetetracycline, e.g., 11a-chloro methacycline. The corresponding alpha-6-deoxytetracycline, e.g., doxycycline, is directly produced in improved yield and purity, and with decreased rhodium consumption.

In a preferred embodiment, a methanolic mixture containing a 6-deoxy-6-demethyl-6-methylenetetracycline, preferably the hydrochloric acid addition salt thereof, triphenylphosphine, hydrochloric acid, and a heterogeneous rhodium catalyst of the invention, is subjected to agitation in a stainless steel autoclave, and hydrogenated at about 90° C. under a hydrogen pressure of about 100 psig. The reaction mixture is cooled to about 60° C. and pumped through a filter to recover the catalyst. To the filtrate is added p-tolune sulfonic acid and the system is stirred at 50°–60° C. for one hour. Thereafter, the system is cooled to 5° C. for at least two hours. The alpha-6-deoxy-5-oxytetracyline p-toluene sulfonate thus obtained is filtered, washed with methanol and then with acetone.

Alternatively, the reductive dehalogenation and hydrogenation can be carried out with a two-step process initially effecting 11a-dehalogenation with a conventional catalyst, e.g., 5% Rh/C or 5% Pd/C in methanol.

The initial catalyst is then removed by filtration, and the solution is again subjected to hydrogenation in the presence of a heterogeneous rhodium catalyst of the invention.

In the following examples, particularly preferred embodiments of the process for the preparation of alpha-6-deoxytetracyclines are described. In the examples, all temperatures are given in Degrees Celsius and all parts and percentages by weight, unless otherwise specified.

EXAMPLE 1

Preparation of Heterogeneous Rhodium Catalyst

Silica gel (20.0 kg) was dried in a vacuum oven at 180° C. for 5 to 6 hours. While stirring, the dried silica gel was added to toluene (100 liters) under a nitrogen blanket. In a separate 15 gallon polypropylene carboy vessel, ethyltriethoxysilyl-2-diphenylphosphine (960 grams) was added to toluene (50 liters) and agitated. The contents of the carboy vessel was then added to the silica gel-containing system and agitated under nitrogen. The system was gently refluxed at 113° C. for 5 hours.

After refluxing, the system was atmospherically distilled (azeotropic) at 110°-115° to remove distillate (100 liters) containing ethanol. Fresh toluene (100 liters) was added to the system with agitation to replace the distillate while cooling to 20°-30° C. The system was filtered to recover a toluene wet cake that was washed with additional toluene.

The cake was added to fresh toluene (140 liters) while agitating under a nitrogen blanket. The mixture was warmed to 55°-70° C. and Wilkinson's Catalyst (880 grams) was added. The system was lightly refluxed at 113° C. under nitrogen for 12 to 16 hours, then cooled to 20°-40° C. The system was filtered to recover the catalyst (23-24 kg) which was washed with toluene and vacuum dried at 45° C.

EXAMPLE 2

Preparation of Doxycycline p-Toluene Sulphonate from Methacycline HCl

Methacycline HCl (13.44 kilograms) was added to methanol (63.0 liters) under a nitrogen blanket. Triphenylphosphine (42 grams) and hydrochloric acid (14 mls.) were added to the system and the system was warmed to 50° C. for about one-half hour. Heterogeneous rhodium catalyst (2.1 kilograms) of Example 1 was added to the system which was pressurized with hydrogen to a pressure of 100 psig. The system was warmed to 90° C. (±5° C.) and maintained at temperature for 24 hours. The system was cooled to 60° C. and pumped to a filter to recover the heterogeneous rhodium catalyst. p-Toluene sulfonic acid (6.16 kilgrams) was added to the system and stirred at 50°-60° C. for one hour. The system was allowed to cool overnight at room temperature and was then cooled to 5° C. for two hours. Doxycycline p-toluene sulfonate was recovered from the system by filtering and was washed with cold methanol (3 liters) and cold acetone (3 liters). The product was dried at about 40° C. The resulting product weighed about 16.0 kilograms (94% theoretical yield). HPLC analysis showed the product to be 99% pure alpha-deoxycline p-toluene sulfonate with no beta epimer present. A second crop of 0.94 kg as sulfosalicylate salt was recovered. The total yield was therefore 99%.

EXAMPLE 3

Preparation of Doxycycline p-Toluene Sulfonate 11a-chloro-6-deoxy-6-demethyl-6-methylene-5oxytetracycline p-toluene sulfonate (25 grams) and triphenylphosphine (10.2 grams) were added to a hydrogenation vessel. Methanol (75 mls.) was added to the mixture, the reactants were warmed to 50° C., and heterogeneous rhodium catalyst of Example 1 (3.0 grams) was added. The reactants were hydrogenated at 90° C. under a hydrogen pressure of 100 psig until hydrogen uptake ceased. The system was cooled to 60° C. and the heterogeneous catalyst was filtered from the slurry. p-Toluene sulphonic acid (8.4 grams) was added to the filtrate at 50° C. and the system was stirred for one hour. The system was stored overnight at room temperature and then held at 5° C. for two hours. Doxycycline p-toluene sulfonate was then filtered from the system and washed with cold methanol (20 mls.) and cold acetone (20 mls.). The resulting product weighed 20.5 grams (87%) and HPLC analysis showed: alpha isomer 99%; beta isomer-negligible. A second crop of 1.9 grams as sulfosalicylate salt was obtained. The total yield was therefore 94%.

EXAMPLE 4

Preparation of Doxycycline Hyclate From Doxycycline p-Toluene Sulphonate

Doxycycline p-toluene sulphonate (13 grams) of Example 3 was mixed with acetone (38 mls.) and water (1.78 mls.) to obtain a solution at 35° C. Nuchar G-60 (1 gram) was added to the system and stirred for one-half hour. The slurry was then filtered through a celite pad. To the filtrate was added ethanol (28.6 mls.) and 18% HCL in ethanol (14.3 mls.). Within ten minutes seed began to appear in the solution. The solution was stirred for three hours at room temperature and then filtered to obtain a cake. The cake was washed first with ethanol (30 mls.), then with acetone (15 mls.) and then dried. The yield of doxycycline hyclate from this first crop was 8.3 grams (76%). HPLC analysis showed the product to be 99.4% pure alpha-doxycycline hyclate with no detectable beta-doxycycline hyclate. A second crop of doxycycline hyclate yielded an additional 2.04 grams, also essentially pure alpha-doxycycline hyclate, giving a total yield of about 95%.

EXAMPLE 5

Preparation of Doxycycline p-Toluene Sulfonate from Methacycline Hydrochloride

Purified methacycline hydrochloride (5.0 grams), concentrated hydrochloric acid (37%; one drop), and methanol (30 mls.) were added to a bomb. The system was placed under a nitrogen atmosphere. Triphenylphosphine (20 mgs.) and heterogeneous rhodium catalyst of Example 1 (1.3 grams) were added to the system. The system was heated to about 90% (ranging from 87.0°-95.0° C.) and hydrogenated under a hydrogen pressure of 119.0 psig at zero time. The hydrogenation extended for 17 hours at which time the hydrogen pressure was about 108.5 psig.

The system was then cooled to 55° C. and decanted to separate a clear supernatant from the silica-supported rhodium catalyst. p-Toluene sulfonate acid hydrate (2.2 grams) was added to the supernatant and the system was warmed to about 50° C. The system was stirred for about two hours at room temperature, stirred in an ice bath for an additional two hours, and then filtered. The recovered cake was washed with cold acetone. The resulting doxycycline p-toluene sulfonate (dry) weighed about 6.2 grams (96.4% yield) and analysis by paper-gram showed only alpha isomer present. A second crop of 2.1 grams was obtained as sulfosalicylate salt. The total yield was therefore 99.3%.

Having thus described the invention, what is claimed is:

1. In a process for the preparation of an alpha-6-deoxytetracycline by the hydrogenation of a substrate selected-6-methylenetetracycline, a 6-deoxy-6-demethyl-6-methylene-tetracycline and salts thereof, the improvement comprising conducting the hydrogenation in the presence of a silica-supported heterogeneous rhodium catalyst prepared by:

(a) reacting a silica gel support with an alkoxysilyl-substituted alkyldiphenyl phosphine of the formula $(EtO)_m(CH_3)_{3-m}Si(CH_2)_nPPh_2$ wherein Et is ethyl;
m is an integer from 1 to 3;
n is an integer from 1 to 6; and
Ph is phenyl, the phosphine having one or more groups capable of functioning as ligands bonding rhodium complexes thereto;

(b) removing ethanol formed by interaction of the alkoxysilyl groups of the phosphine with hydroxyl groups on the surface of the silica gel; and (c) bonding the resulting reaction product to a rhodium complex selected from the group consisting of $Rh_2Cl_2(C_2H_4)_4$, $Rh_2Cl_2$ (cyclooctene)$_4$, $RhCl_2(PPh_3)$, and $Rh(PPh_3)_3Cl$, such that the resulting silica-supported heterogeneous rhodium catalyst contains from 0.3 to 0.6% rhodium.

2. The process of claim 1 for producing doxycycline, wherein the substrate is 11a-chloro methacycline, methacycline, or an acid addition salt thereof.

3. The process of claim 1, wherein the substrate is a 6-methylenetetracycline.

4. The process of claim 1, wherein the substrate is a 11a-chloro-6-methylenetetracycline.

* * * * *

UNITED STATES PATENT AND TRADEMARK OFFICE
CERTIFICATE OF CORRECTION

PATENT NO. : 5,049,683

DATED : September 17, 1991

INVENTOR(S) : George Krsek

It is certified that error appears in the above-identified patent and that said Letters Patent is hereby corrected as shown below:

In the Abstract:   Change "catalyst:" to --catalyst.--;
delete the formula

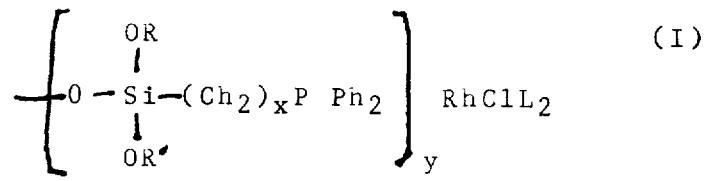   (I)

Column 2, Lines 40-44:   Delete the formula

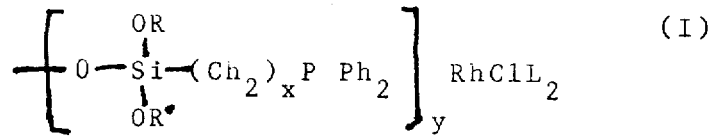   (I)

Column 4, line 5:   Change "$(EtO)_3Si(CH_2)_2PPh_2$" to --$(EtO)_3Si(CH_2)_3PPh_2$--.

Column 5, line 9: Change "$Rh_2cl_2(cyclooctene)_4$" to --$Rh_2Cl_2(cyclooctene)_4$--.

Column 5, line 24: Change "(II)" to --(I)--.

UNITED STATES PATENT AND TRADEMARK OFFICE
CERTIFICATE OF CORRECTION

PATENT NO. : 5,049,683

DATED : September 17, 1991

INVENTOR(S) : George Krsek

It is certified that error appears in the above-identified patent and that said Letters Patent is hereby corrected as shown below:

Column 5, line, 37 change "(III)" to --(II)--.

Column 6, line 59 change "p-tolune" to --p-toluene--.

Column 7, line 52 insert --this-- after "at".
line 59 change "p-tolune" to --p-toluene--.

Column 9, lines 11-12 change "selected-6-methylenetetracycline" to --selected from the group consisting of an 11a-chloro-6-deoxy-6-demethyl-6-methylenetetracycline--.

Signed and Sealed this

Sixth Day of April, 1993

*Attest:*

STEPHEN G. KUNIN

*Attesting Officer*   Acting Commissioner of Patents and Trademarks